(12) United States Patent
El-Rafaey

(10) Patent No.: US 6,664,290 B1
(45) Date of Patent: *Dec. 16, 2003

(54) ORAL OR VAGINAL ADMINISTRATION OF MESOPROSTOL IN THIRD STAGE LABOR

(75) Inventor: Hazem El-Rafaey, London (GB)

(73) Assignee: University College London, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1122 days.

(21) Appl. No.: 08/809,379

(22) PCT Filed: Sep. 26, 1995

(86) PCT No.: PCT/GB95/02277

§ 371 (c)(1),
(2), (4) Date: Apr. 15, 1997

(87) PCT Pub. No.: WO96/09825

PCT Pub. Date: Apr. 4, 1996

(30) Foreign Application Priority Data

Sep. 27, 1994 (GB) .............................................. 9419566

(51) Int. Cl.[7] .............................................. A61K 31/215
(52) U.S. Cl. ...................................... 514/530; 514/935
(58) Field of Search ................................. 514/530, 935

(56) References Cited

PUBLICATIONS

HCAPLUS abstract, AN 1987:569413 (Gullikson et al.), 1987.*

HCAPLUS abstract, AN 1986:180656 (Lacy), 1986.*

HCAPLUS abstract, AN 1985:606215 (Cohen et al.), 1985.*

Facts and Comparisons Olin et al., St. Louis, Mo.: J.B. Lippincott, pp. 117h, 118, and 1182, Feb. 1990.*

Campos P., G.A. et al., "Misoprostol–Un Analogo de la PGE1–Para La Induction de Parto a Termino: Estudio Comparativo y Randomizado con Oxitocina," *Rev. Chil. Obstet. Ginecol.* 1994, 59 (3), 190–196.

Fletcher, H., "Intravaginal Misoprostol Versus Dinoprostone as Cervical Ripening and Labor–Inducing Agents," *Obstet. and Gyn.* 1994, 83(2), 244–247.

Kelsey, J.J. et al., "Drug Therapy during Labor and Delivery," *Am. J. Hosp. Pharm.* 1994, 51, 2394–2505.

Qian, Y. et al., "Potent Contratile Actions of Prostanoid $EP_3$–Receptor Agonists on Human Isolated Pulmonary Artery," *Br. J. Pharm.* 1994, 133(2), 369–374.

Sanchez–Ramos, L. et al., "Labor Induction with the Prostaglandin $E_1$ Methyl Analogue Misoprostal Versus Oxytocin: A Randomized Trial," *Obstet. and Gyn.* 1993, 81 (3), 332–336.

Sanchez–Ramos, L. et al., Letter to the Editor, *Obstet. and Gyn.* 1994, 83 (5), 799–801.

* cited by examiner

*Primary Examiner*—Theodore J. Criares
(74) *Attorney, Agent, or Firm*—Licata & Tyrrell P.C.

(57) ABSTRACT

This invention relates to a method of limiting postpartum hemorrhage comprising administering orally a single effective dose of misoprostol to a woman during the third stage of labor.

2 Claims, No Drawings

ORAL OR VAGINAL ADMINISTRATION OF MESOPROSTOL IN THIRD STAGE LABOR

This application is a 371 of PCT/GB95/02277 filed Sep. 26, 1995.

The present invention relates to the use of an alternative pharmaceutical agent in the place of Syntometrine and ergometrine for routine prevention of bleeding during or immediately after the third stage of labour. It is generally accepted that the advantages of the use of the aforementioned drugs outweigh their disadvantages and hence they are routinely administered to all women in Europe and North America immediately after delivery unless specifically contraindicated. No equally effective acceptable alternative has been introduced to the obstetric practice since these drugs were first described almost 60 years ago. I have found that Misoprostol, a drug that is widely marketed for the treatment of stomach ulcers, can fulfil the requirements of an effective agent that can be used routinely for that purpose.

The third stage of labour is potentially the most hazardous part of labour for the mother. The main risk is that of postpartum haemorrhage (PPH) with its subsequent morbidity. The rise of oxytocic drugs for the prevention of PPH has been regarded as one of the most enduring advances in medical science. The intramuscular administration of syntometrine (a combination of 5 i.u. syntocinon with 0.5 mg of Ergometrine) after the delivery of the fetus is widely practised in the developing world and has become known as the active management of the third stage of labour.

The prophylactic use of oxytocics in the third stage of labour is of particular relevance to obstetrics practice in the third world where atonic postpartum haemorrhage is a common event due to high multiparity, prolonged labour and fibroid uterus. Maternal death due to PPH is reported to be between 17 and 40% in some parts of the word (World Health Organisation 1989 and 1991). Postpartum haemorrhage is the single most common cause of maternal death in the developing world.

The concept of actively managing the third stage of labour, like many other interventions in the managements of labour, has been challenged in recent years. The first large randomised study performed in this field has shown that the routine use of syntometrine in the third stage of labour has been shown to reduce the incidence of PPH from around 18% to 5% and to reduce the length of the third stage of labour from fifteen minutes to five minutes. Further, it has been shown to reduce the need for therapeutic oxytocics from 30% to 6%. An overview of trials performed in this field strongly suggests that the routine prophylactic use of an oxytocic in the third stage of labour reduces the incidence of PPH. Despite this important problems remain.

Syntometrine is an effective combination administered by the intramuscular route, the syntocinon acting in about 2.5 minutes and the Ergometrine producing a more sustained uterotonic contraction five minutes later. However, Syntometrine is contraindicated in women with high blood pressure in pregnancy. An estimated 15% of women are therefore denied the beneficial effects of Syntometrine in the third stage of labour.

The advantages of using Syntometrine must be considered with the rare but serious side effects attributed to their hypertensive properties. Syntometrine has been known to produce a rise in blood pressure in women previously known to be normotensive. Maternal death from cardiac arrest and intracerebal haemorrhage have been attributed to Ergometrine, as have non-fatal instances of cardiac arrest and myocardial infarction. Syntometrine has also been known to be commonly associated with gastrointestinal side effects in the form of nausea and vomiting which can reduce patient acceptability.

Active management of a third stage of labour is not a universal practice. In many parts of the world, the routine use of oxytocic agents is not a practical option for various other reasons. First, oxytocic agents are not stable at high ambient temperatures and therefore require special storage requirements, for example refrigeration, over prolonged periods, Syntometrine has to be stored between 2° and 8° C. and protected from light. Although Syntometrine may be stored at temperatures up to 25° C. for two months when protected from light, activity tends to decline. One study investigated the stability of Ergometrine and Methyl Ergometrine after one year of suboptimal storage which showed that 90% of the therapeutic activity of the drugs was lost over that period. The results are similar when the drug is stored in brown vials.

These requirements represent an important hurdle to the wider use of oxytocics in the developing world and accordingly, the feasibility of synthesizing forms of the drugs which are able to withstand high temperatures was considered by the World Health Organisation, (WHO) without a successful candidate being available to date.

Secondly, active management of the third stage of labour is also compromised in the third world situations because of the unknown status of the mother. Often mothers present to clinics in an advanced stage of labour when the doctor is unable to assess the likely hitherto hypertensive status of the mother and indeed is likely to be faced with difficult decisions of a more immediate nature. Because of this, oxytocics are not routinely administered, even if available in case their administration exacerbates latent hypertension.

Further, the prevalence of Hepatitis C, AIDS and other blood born diseases, in third world countries means that drugs are administered by injection only if there is no practical alternative.

Accordingly in order to find a suitable replacement for active management of the third stage of labour, a drug must have the following properties.

1. Storable at ambient temperatures with a long shelf-life.
2. Capable of stopping bleeding postpartum at low dosages and without significant side effects.
3. Having a rapid onset action.
4. Administrable by the oral or vaginal route so as to be routine for prophylaxis.
5. Have the same or an enhanced efficacy with regard to prevention of PPH and
6. Non-hypertensive or better still slightly hypotensive.

Misoprostol originally formed the subject of GB-A-1492426 which relates to synthetic 15-deoxy-16-hydroxy-16-methyl analogues of naturally occurring prostagladin $E1^5$, of the formula (1)

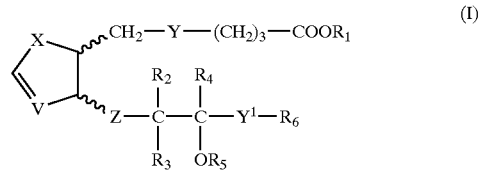

wherein $R_1$, $R_2$ and $R_3$ are hydrogen or an alkyl radical containing from 1 to 7 carbon atoms; $R_4$ is an alkyl radical containing from 1 to 7 carbon atoms; $R_5$ is hydrogen, an alkyl radical containing from 1 to 7 carbon atoms or an alkanoyl radical containing from 1 to 7 carbon atoms; $R_6$ is an alkyl radical containing from 2 to 4 carbon atoms or a cycloalkyl radical containing from 5 to 7 carbon atoms; X is carbonyl or hydroxymethylene; V is methylene, hydroxymethylene or alkanoyloxymethylene wherein the alkanoyl radical contains from 1 to 7 carbon atoms; or, when X is carbonyl, V may also be a radical of the formula

in which the bond represented by the dotted line in the general formula is present; Y is ethylene or vinylene; Y' is vinylene, ethynylene or the group

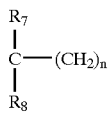

wherein n is 0 or 1 and $R_7$ and $R_8$ are hydrogen or an alkyl radical containing from 1 to 7 carbon atoms; Z is ethylene, vinylene or ethynylene; the wavy lines represent the alternative α or β sterochemical configuration or the epimeric mixture.

Our invention relates therefore to orally or vaginally administered protagladins which have significant utertonicity without adverse side effects, are rapidly absorbed orally or from a suppository via the vaginal route, are quick acting and thermostable in storage. Drugs of this type of which the prostagladin E1[5] analogues are preferred examples are particularly efficacious, Misoprostol itself is merely the most preferred.

Misoprostol is available under the tradename Cytotec and has been known for several years for oral administration for the healing of duodenal and gastric ulcers; including those induced by non-steroidal anti-inflammatory drugs; (NSAID).

Cytotec protects gastroduodenal mucosa by inhibiting basal, stimulated and nocturnal acid secretion; by reducing the volume of the secretion, by reducing proteolytic activity of the gastric fluid, and by increasing bicarbonate and mucosal secretion.

Cytotec is contraindicated in pregnancy because it may cause intermenstrual bleeding in pre-menopausal women. The normal oral dose is 200 µg, four times a day, for use in ulcer therapy. Preclinical animal studies have shown that the drug had no effect on the uterus. However, Misoprostol has been used, without the benefit of medical intervention, in very large doses per os in Latin America as an abortifactant and lately its utertonic effects have been discussed. Prostagladins in general have been used in obstetrics for at least two decades and are widely used, often with other agents, for cervical ripening, induction of labour and induction of abortion. Some injectable prostagladins have also been used as a last resort in the treatment of critically. ill patients with intractable postpartum haemorrhage.

A prostagladin $F_2A$ has in fact already been used in one trial in 1979 to assess the efficacy of its prophylactic use in the third stage of labour. As this prostagladin can only be administered by direct injection into the uterine muscle (intramyometrially) it is inappropriate to recommend such an invasive approach for general use. Further, this group of prostagladins is associated with unacceptable side effects such that its use is only suitable in life threatening situations.

Misoprostol and its immediate analogues set out above, is an E1 prostagladin analogue which may be administered orally. Its safety is well established in the prevention and management of peptic ulcer disease.

Misoprostol has been shown in animal studies to possess a mild hypotensive effect at about 800 µg in a single dose whereas at about 400 µg, patients remain substantially normotensive.

As stated above, unlike oxytocic agents, I have now shown that Misoprostol and similar prostagladin analogues when administered to humans are not hypertensive up to dosages of 800 µg and accordingly, by virtue of their strong utertonic features, they have an apparent superiority in the management of postpartum haemorrhage and appear to be ideal agents for prophylactic use in the third stage in labour. With regard to Misoprostol in itself; Misoprostol is already marketed as tablets for oral use, does not require special storage conditions and is known to possess a shelf-life of several years.

Accordingly therefore to the present invention there is provided the use in the manufacture of a drug for prophylactic treatment of mothers in the third stage of labour of an orally or vaginally administrable active principal selected from a quick acting thermostable prostagladin analogue with significant uterotonicity disposed in a pharmaceutically acceptable carrier or diluent therefor. In particular, this compound may be selected from a synthetic 15-deoxy-16-hydroxy-16-methyl analogue of an naturally occurring protagladin E1[5] and particularly from a compound of the formula I given above for example Misoprostol.

In particular, this compound may be selected from racemic methyl 7-[3(R)-hydroxy-2β-(4(RS)-4-hydroxy-4-methyl-trans-1-octenyl)-5-oxocyclopentane]-1α-heptanoate; racemic methyl 7-[3(S)-hydroxy-2β-(4(RS)-4-hydroxy-4-methyl-1-octynyl)-5-oxocyclopentane]-1α-heptanoate; and racemic methyl 7-[3(R)-hydroxy-2β-(4(RS)-4-cyclohexylmethyl-4-hydroxy-4-methyl-trans-1-butenyl)-5-oxocyclopentane]-1α-heptanoate. The active principal may be administered orally in an amount of 200–800 µg and preferably in an amount of about 400 or 600 µg; immediately after the second stage of labour. The diluent or carrier may be conventional and adapted to release the active principal to the contents of the stomach or intestine, or may be in the form of a suppository or pessary in accord with normal pharmacological practice.

The active principal may be administrable orally in an amount of 100–800 µg and preferably in an amount of 400 to 600 µg as a single dose administered at the commencement of the third stage of labour. The diluent or carrier may be any conventional diluent or carrier which is adapted to release the active principal sublingually into the contents of the stomach to achieve rapid onset. Misoprostol itself is particularly efficacious in the foregoing respects since pharmokenetic studies have shown that Misoprostol under goes extensive metabolism during and/or prior to its gastro intestinal absorption. Several metabolites are formed and no unchanged drug is detected in the plasma or urine after use. The biologically active metabolite in the plasma is Misoprostol acid, the absorption of Misoprostol and/or Misoprostol acid is extremely rapid resulting the peak plasma levels at less than fifteen minutes. The results are substantially the same if the drug is administered vaginally.

The invention will now be described by way of illustration only in the following example:

Patients and Methods

The study protocol was reviewed and approved by the local Ethics Committee. Information sheets explaining the aims of the trial were distributed to potential participants either in the antenatal classes, antenatal clinics, and the Day Assessment Area. On admission to labour ward women were reminded about the trial and a written informed consent was obtained if they still wished to participate in the study.

The main objective of this study was to estimate the incidence of primary postpartum haemorrhage (PPH). This was defined as estimated blood loss of or more than 500 ml. Other measures of blood loss were also considered e.g. severe PPH i.e. >1000 ml; secondary PPH (after 24 hours); need for blood transfusion; use of therapeutic oxytocics (i.e. the need for extra oxytocics); length of third stage; incidence of manual removal of placenta; the need for subsequent evacuation of the retained products of conception; and the change in haemoglobin and packed cell volume in those who had instrumental delivery and/or who had blood loss of 500 ml or more compared to the Haemoglobin done late in pregnancy. Potential adverse effects of the drug used were also recorded e.g. incidence of vomiting, diarrhoea, shivering and hypertension (defined as diastolic blood pressure >100 or Systolic Blood pressure >150). All of these measures were documented by the midwife on call on a specially designed form with demographic information and information related to the type and circumstances of delivery.

The principle criteria for exclusion were: placenta praevia, multiple pregnancy, intrauterine death, gestational age less than 32 weeks gestation, women with previous PPH and women in their sixth pregnancy or more. In this pilot study, women with hypertension, preeclampsia or pregnancy induced hypertension were also excluded.

Immediately after delivery of the baby and clamping and dividing the cord, patients were asked to swallow 600 μg Misoprostol (3 tablets). Syntometrine was not given but midwives were instructed to do so if they felt there was a clinical indication. Otherwise the delivery of the placenta was managed according to hospital policy (active management policy). Blood loss was estimated clinically by the attendant midwife or obstetrician. A sample of venous blood was obtained two days later after birth for haemoglobin and packed cell volume assessment from women who had instrumental delivery or from those who had blood loss of 500 ml or more. A record was kept of the last recorded blood pressure and temperature before birth and one hour after delivery.

Statistical Methods

Categorical variables are summarised as numbers and percentages, whereas continuous variables that are normally distributed are presented as means and standard deviations (SD), continuous variables that are not normally distributed are presented as medians and interquartile ranges (IQR). Comparisons between the systolic, diastolic blood pressure, haemoglobin, haematocrit and temperature before and after delivery were conducted via the paired t-test. Association between two categorical variables was assessed via Chi-square testing. The significance level was set to the 5% level.

Results

Two hundred and thirty seven patients with mean age (SD) of 29.1 (5.8) years, were recruited to the study. The demographic characteristics and labour variables of these patients are summarised in Table 1. One hundred and thirteen patients (48%) were primigravidae. 47 (20%) patients had induction of labour, whereas overall 72 (30%) required syntocinon augmentation. Episiotomy was performed for 52 (22%) patients. 107 (45%) patients had a 1st or 2nd degree tears. Epidural anaesthesia was used by 112 (47%) of these patients.

The placenta was delivered spontaneously in all cases apart from four cases (2%) where manual removal of the placenta was needed. The median length of the third stage of labour was 5 (IQR of 4 to 7) minutes). 13 (6%) patients had blood loss more than or equal to 500 ml of which only 6 (3%) had a blood loss greater than 500 whereas no patient had a blood loss of 1000 ml or more. Secondary post partum haemorrhage was not reported in any case. The median blood loss for all the study population was 200 (IQR of 150 to 300) ml. Four patients only (2%) required a manual removal of placenta and four had a haemoglobin level of less or equal to 9 g/dl. Blood transfusion was required for 2 patients in this trial, one patient had a broad ligament haematoma that was managed conservatively. The second patient required blood transfusion during manual removal of a retained placenta. The effects of Misoprostol on the third stage of labour and its side effects are summarised in Table 2.

Gastrointestinal side effects were infrequent. Vomiting occurred in 19 (8%) patients during the first hour after delivery and loose stool was reported by seven (3%) patients during the first 24 hours after delivery. These were usually mild and did not necessitate any treatment. The occurrence of shivering was on the other hand reported by 148 (62%) patients. This was self-limiting and lasting for around 10–15 minutes twenty minutes are swallowing the tablets. There was no cases of infection and no patient required surgical evacuation of retained products of conception.

The last measured systolic and diastolic blood pressure before delivery was compared to that measured one hour after delivery. A mean reduction of 1.0 (SE=0.9) and 0.8 (0.6) mm Hg respectively were observed but neither were not statistically significant. Similarly, haemoglobin, haematocrit and temperature were compared before and after delivery. All are summarised in Table 3. A reduction of 0.3 (0.15) g/l of the haemoglobin end of 0.01 (0.005) of the haematocrit were marginally significant (p–0.006 and p=0.047). Temperature increased significantly by 0.5 (0.005 (C°(p=0.001).

This report has shown that the third stage of labour can be successfully managed with Misoprostol. The incidence of postpartum haemorrhage (6%), need for further therapeutic oxytocics (5%) and the length of the third stage of labour (median 3 minutes) in this study is considerably lower than those reported when the third stage is managed physiologically and comparable to that obtained by syntometrine. The success has been achieved with a simple oral medication.

The routine prophylactic administration of an oxytocic agent is an integral part of the active management of labour and has been shown to reduce the incidence of post partum haemorrhage from 18% to 5%, to reduce the length of the third stage of labour from 15 minutes to 5 minutes and the need for therapeutic oxytocics from 30% to 6%. An overview of trials performed in this field strongly suggest that routine use of oxytocics in the third stage of labour reduces the incidence of PPH. The advantages of prophylactic syntometrine must be considered together with the rare but serious morbidity which has been attributed to its hypertensive effect. The hypertensive effect was apparent when syntometrine was compared to Syntocinon; Syntometrine was found to increase the incidence of hypertension (diastolic blood pressure more than 100 mm/Hg) by 5 fold. Maternal death from cardiac arrest and intracerberal haemorrhage have been attributed to this direct pharmacological effect, as have non-fatal instances of cardiac arrest and myocardial infection. Due to the pilot nature of the present study, we excluded patients with high blood pressure from the trial, nevertheless we could not identify any hypertensive effects of Misoprostol on women who were normotensive before labour.

Women who express dissatisfaction with the conventional management of the third stage of labour report that vomiting in particular is the most distressing symptom they had to endure. The incidence of vomiting reported in this study is almost half that reported when syntometrine is used. In this study, however we identified a side effect of Misoprostol that has not been described hitherto. Shivering occurred in 62% of patients and was generally regarded as a nuisance rather than as a serious problem. In the field of abortion, the use of larger Misoprostol dosages was not associated with this side effect. Its occurrence therefore was only identified during the prepilot work leading to this study. Shivering is a recognised symptom after normal delivery and its incidence increases in association with regional anaesthesia. During epidural anaesthesia, the incidence of shivering is between 33–60%. This should be compared with an incidence of 10% during normal labour without epidural anaesthesia. In this study the incidence of shivering was 62%, there was no significant difference between patients who had epidural anaesthesia and those who had not. It seems however that shivering is dose related and may be significantly reduced without loss of efficacy by reducing the dosage of active ingredient to 400 µg.

The prophylactic use of oxytocics in the third stage of labour is of particular relevance to the obstetric practice in the third world where atonic postpartum haemorrhage is a common event due to high multiparity, prolonged labour and fibroid uterus. Death due to postpartum haemorrhage is said to represent between 17–40% of maternal mortality in some parts of the world. The availability of an oral and thermostable preparation for routine management of the third stage of labour will have considerable implications for obstetric practice in developing countries. The implications are considerable since if this approach became standard practice, the management of the third stage of labour would be simpler, potentially safer and more acceptable to women and their attendants alike everywhere.

TABLE 1

Demographic Characteristics and Labour Variables of the Recruited Study Population

|  | n = 237 |
| --- | --- |
| Demographic variables: | |
| Mean (SD) maternal age (year) | 29.1 (5.8) |
| Mean (SD) maternal weight (kg) | 76.3 (11.5) |
| Mean (SD) maternal height (cm) | 163.2 (6.7) |
| Number (%) of primigravidae | 113 (48%) |
| Mean (SD) of gestational age at delivery (week) | 39.7 (1.4) |
| Labour variables: | |
| Number (%) with spontaneous onset | 190 (80%) |
| Number (%) with Syntocinon augmentation | 72 (30%) |
| Number (%) with epidural in 1st or 2nd stage | 112 (47%) |

TABLE 1-continued

Demographic Characteristics and Labour Variables of the Recruited Study Population

|  | n = 237 |
| --- | --- |
| Number (%) with narcotic analgesia in 1st or 2nd stage | 90 (38%) |
| Number (%) with episiotomy | 52 (22%) |
| Number (%) with 1st, 2nd tear | 106 (45%) |
| Number (%) with Spontaneous cephalic delivery | 179 (72%) |
| Mean (SD) length of 1st stage (hour) | 6.7 (3.9) |
| Mean (SD) length of 2nd stage (min) | 66 (60) |
| Mean (SD) of birthright (KG) | 3.30 (0.5) |

TABLE 2

Effect of Misoprostol on the Management of the Third Labour

|  | n = 237 |
| --- | --- |
| Number (%) with blood loss > = 500 ml | 13 (6%) |
| Number (%) with blood loss > 1000 ml | 0 (0%) |
| Median (IQR) of blood loss (ml) | 200 (150–300) |
| Number (%) with manual removal of placenta | 4 (2%) |
| Number (%) with repeat syntometrine injection | 12 (5%) |
| Number (%) with systolic - 150 (mm Hg) | 2 (1%) |
| Number (%) with diastolic - 100 (mm Hg) | 0 (0%) |
| Number (%) with haemoglobin < 9 (g/l) | 4 (2%) |
| Median (IQR) third stage length (min) | 5 (4–7) |
| Number (%) with third stage length >= 30 minutes | 1 (0.5%) |
| Number (%) who vomited | 19 (8%) |
| Number (%) who had diarrhoea | 7 (3%) |
| Number (%) who had shivering | 148 (62%) |

TABLE 3

Maternal Blood Pressure, Haemoglobin and Temperature Measurements Before and After Delivery (Values are Means (SD))

|  | Before delivery | After delivery | Mean Difference (SE) | P-Value |
| --- | --- | --- | --- | --- |
| Systolic blood pressure (mm Hg) n = 184 | 119.3 (13) | 118.4 (12) | −1.0 (0.9) | 0.25 |
| Diastolic blood pressure (mm Hg) n = 184 | 73.8 (8) | 73.0 (8) | −0.8 (0.6) | 0.20 |
| Haemoglobin (g/l) n = 76 | 11.3 (0.9) | 11.0 (1.3) | −0.3 (0.15) | 0.06 |
| Haematocrit n = 73 | 0.34 (0.03) | 0.33 (0.04) | −0.01 (0.005) | 0.047 |
| Temperature (C.) n = 182 | 36.6 (0.4) | 37.1 (0.7) | 0.5 (0.05) | 0.001 |

What is claimed is:

1. A method of limiting postpartum hemorrhage comprising administering orally a single effective dose of misoprostol to a woman during the third stage of labor.

2. A method of limiting postpartum hemorrhage comprising administering by pessary or suppository a single effective dose of misoprostol to a woman during the third stage of labor.

* * * * *